(12) United States Patent
Pascolo

(10) Patent No.: US 10,729,785 B2
(45) Date of Patent: *Aug. 4, 2020

(54) PARTICLES COMPRISING PROTAMINE AND RNA IN COMBINATION WITH ENDOSOME DESTABILIZING AGENTS

(71) Applicant: BioNTech SE, Mainz (DE)

(72) Inventor: Steve Pascolo, Zurich (CH)

(73) Assignee: BioNTech SE, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/309,686

(22) PCT Filed: May 19, 2014

(86) PCT No.: PCT/EP2014/060236
§ 371 (c)(1),
(2) Date: Nov. 8, 2016

(87) PCT Pub. No.: WO2015/176737
PCT Pub. Date: Nov. 26, 2015

(65) Prior Publication Data
US 2017/0151349 A1    Jun. 1, 2017

(51) Int. Cl.
| | | |
|---|---|---|
| *A61K 48/00* | (2006.01) | |
| *C12N 15/88* | (2006.01) | |
| *A61K 47/69* | (2017.01) | |
| *A61K 47/58* | (2017.01) | |
| *A61K 47/64* | (2017.01) | |
| *A61K 9/16* | (2006.01) | |
| *A61K 38/17* | (2006.01) | |
| *A61K 41/00* | (2020.01) | |
| *A61K 47/32* | (2006.01) | |
| *A61K 47/42* | (2017.01) | |

(52) U.S. Cl.
CPC ........ *A61K 48/0008* (2013.01); *A61K 9/1694* (2013.01); *A61K 38/1709* (2013.01); *A61K 41/0057* (2013.01); *A61K 47/32* (2013.01); *A61K 47/42* (2013.01); *A61K 47/585* (2017.08); *A61K 47/645* (2017.08); *A61K 47/6921* (2017.08); *C12N 15/88* (2013.01); *C12N 2760/16033* (2013.01); *C12N 2760/16122* (2013.01); *C12N 2760/16131* (2013.01); *Y02A 50/463* (2018.01)

(58) Field of Classification Search
CPC . A61K 48/00089; C12N 15/11; C12N 11/087
See application file for complete search history.

(56) References Cited

U.S. PATENT DOCUMENTS

| | | | | |
|---|---|---|---|---|
| 5,547,932 | A * | 8/1996 | Curiel | A61K 47/6901 435/456 |
| 7,514,400 | B2 * | 4/2009 | Peterson | C07K 5/0202 514/1.1 |
| 7,737,108 | B1 | 6/2010 | Hoffman et al. | |
| 8,889,631 | B2 * | 11/2014 | Peterson | A61K 47/48338 514/1.2 |
| 2004/0023902 | A1 * | 2/2004 | Marasco | A61K 48/00 514/44 R |
| 2005/0025821 | A1 * | 2/2005 | Harvie | A61K 9/1272 424/450 |
| 2010/0160216 | A1 | 6/2010 | Hoffman et al. | |
| 2010/0286378 | A1 * | 11/2010 | Li | C12N 15/111 536/23.1 |
| 2011/0123637 | A1 | 5/2011 | Pascolo | |
| 2014/0134232 | A1 * | 5/2014 | Boulikas | A61K 9/1271 424/450 |

FOREIGN PATENT DOCUMENTS

| | | | |
|---|---|---|---|
| WO | WO 2009/120247 A2 | 10/2009 | |
| WO | WO-2009144230 A1 * | 12/2009 | ........... A61K 9/5169 |
| WO | WO 2010/129023 A2 | 11/2010 | |

OTHER PUBLICATIONS

He et al. Therapeutic Delivery 4 1499-1510, 2013 (Year: 2013).*
Summerton et al. Ann N.Y. Acad. Sci. 1058: 62-75 (Year: 2005).*
Kakudo et al. Biochemistry 43, 5618-5628 (Year: 2004).*

* cited by examiner

*Primary Examiner* — Brian Whiteman
(74) *Attorney, Agent, or Firm* — DLA Piper LLP (US)

(57) ABSTRACT

The present invention relates to particles comprising protamine, RNA and at least one endosome destabilizing agent, to methods of their production and to pharmaceutical compositions or kits containing the particles. It further relates to particles comprising protamine and RNA for use in methods of treatment or prevention of diseases and to kits comprising such particles together with at least one endosome destabilizing agent.

15 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Peptide 1

<400> SEQUENCE: 1

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 2
<211> LENGTH: 34
<212> TYPE: PRT
<213> ORGANISM: Artificial Sequence
<220> FEATURE:
<223> OTHER INFORMATION: Peptide 2

<400> SEQUENCE: 2

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys
```

PARTICLES COMPRISING PROTAMINE AND RNA IN COMBINATION WITH ENDOSOME DESTABILIZING AGENTS

CROSS-REFERENCE TO RELATED APPLICATIONS

This application is a 35 USC § 371 National Stage application of International Application No. PCT/EP2014/060236 filed May 19, 2014, now pending. The disclosure of each of this application is considered part of and is incorporated by reference in the disclosure of this application.

TECHNICAL FIELD OF THE INVENTION

The present invention relates to particles comprising protamine, RNA and at least one endosome destabilizing agent, to methods of their production and to pharmaceutical compositions or kits containing the particles. It further relates to particles comprising protamine and RNA for use in methods of treatment or prevention of diseases and to kits comprising such particles together with at least one endosome destabilizing agent.

BACKGROUND OF THE INVENTION

Introducing foreign gene information in the form of RNA or DNA into cells can be achieved for example by using liposomal and non-liposomal formulations or by physical methods such as electroporation. Although these methods are broadly used for research purposes, pharmaceutical delivery of nucleic acids in vivo remains a challenge as formulations such as liposomes are often found to be unstable and/or toxic.

The present inventor has previously established conditions allowing the production of particles of different sizes (ranging from 50 nm up to micrometers in average) by mixing together protamine and RNA in defined salt conditions/concentrations/protamine-RNA ratios (Rettig L. et al.; WO 2009/144230 A1). The inventor and others have reported that these formulations can be taken up by cells including immune cells and signal though endosome resident receptors, namely Toll Like Receptors (TLRs), particularly TLR-7 and -8, thereby leading to modular immunostimulation (Rettig et al.; Fotin-Mleczek et al.). However, when messenger RNA (mRNA) was used to generate the particles within the adequate mass ratios, i.e. protamine:RNA=1:2 or higher, the mRNA was not expressed (not translated) in the cells that took up particles. In particular, it has been demonstrated by Fotin-Mleczek et al. that "the complexation process itself can inhibit the translation of mRNA and abolish antigen expression". The authors conclude that "translability and immune stimulating activity are antidromic in protamine:mRNA complexation of different ratios". They report that a protamine-RNA mass ratio above 1:2 generates immunostimulating particles (stimulation through TLRs) that are translation-incompetent. These results suggest that, due to its high compaction, no functional RNA can be released from protamine particles made at a protamine:RNA ratio above 1:2.

Therefore, there is a need for particles comprising protamine and RNA, in particular particles comprising protamine and RNA at a protamine:RNA ratio above 1:2, which allow the RNA to be efficiently released and to be functional within the cell.

SUMMARY OF THE INVENTION

In a first aspect, the present invention relates to a particle comprising protamine, RNA and at least one endosome destabilizing agent (EDA).

In one embodiment, the protamine:RNA mass ratio is in the range of from 16:1 to 1:2, preferably in the range of from 8:1 to 1:2, more preferably in the range of from 4:1 to 1:2.

In one embodiment, the particle has a size in the range of from 10 nm to 990 nm, preferably of from 50 nm to 990 nm. In another embodiment, the particle has a size in the range of from 10 nm to 450 nm, preferably of from 50 nm to 450 nm. In yet another embodiment, the particle has a size in the range of from 450 nm to 990 nm.

In one embodiment, the EDA is selected from the group consisting of organic and inorganic molecules, polymers, lipids, inorganic nanoparticles and peptides.

In one embodiment, the endosome destabilizing activity of the EDA is triggered by an external stimulus.

In one embodiment, the EDA is a pH-reactive agent.

In one embodiment, the endosome destabilizing activity of the pH-reactive agent is triggered by exposure to a pH in the range of from 4.0 to 6.5, preferably in the range of from 4.5 to 6.0, more preferably in the range of from 4.5 to 5.5.

In one embodiment, the pH-reactive agent is selected from the group consisting of polymers and peptides, wherein, preferably, the polymers are polymers of acrylic acid or substituted acrylic acid, and the peptides are hemagglutinin-derived peptides. In one embodiment, the hemagglutinin-derived peptides are Influenza hemagglutinin-derived peptides.

In one embodiment, the EDA is a photosensitizer.

In one embodiment, the endosome destabilizing activity of the photosensitizer is triggered by exposure to light.

In one embodiment, the photosensitizer is selected from the group consisting of porphyrins, phthalocyanines, purpurins, chlorins, benzoporphyrins, lysomotropic weak bases, naphtalocyanines, cationic dyes, tetracyclines, pheophorbides, and derivatives or isomers thereof, wherein, optionally, the photosensitizer is conjugated to a carrier molecule.

In one embodiment, the RNA is selected from the group consisting of messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers, preferably from the group consisting of mRNA, siRNA, shRNA, miRNA, antisense RNA, isRNA and RNA aptamers.

In a further aspect, the present invention relates to a method for the preparation of particles, the method comprising the steps of:
  (a) providing a solution of protamine;
  (b) providing a solution of RNA;
  (c) providing a solution of at least one endosome destabilizing agent (EDA); and
  (d) combining the solutions obtained in steps (a) and (b) and adding the solution obtained in step (c).

In another aspect, the present invention relates to a pharmaceutical composition or kit comprising the particle as defined above and optionally one or more pharmaceutically acceptable carriers, diluents and/or excipients.

In a further aspect, the present invention relates to the particle as defined above or the pharmaceutical composition or kit as defined above for use in a method of treatment or prevention of a disease or for use in a method of immunostimulation.

In a further aspect, the present invention relates to a particle comprising protamine and RNA for use in a method of treatment or prevention of a disease or for use in a method of immunostimulation, the method comprising the steps of:
(a) administering the particle to a subject in need thereof; and
(b) administering at least one endosome destabilizing agent (FDA) to the subject and/or exposing the subject to an external stimulus which triggers the endosome destabilizing activity of the EDA or which destabilizes endosomes.

In one embodiment, the EDA is administered before or after the particle, preferably after the particle.

In one embodiment, the particle and the EDA are administered by different routes, wherein, preferably, the particle is administered systemically and the EDA is administered topically, or vice versa.

In one embodiment, the EDA is administered simultaneously with the particle, wherein, preferably, the EDA and the particle are administered by the same route.

In one embodiment, the EDA is as defined above.

In one embodiment, the external stimulus is a localized external stimulus.

In one embodiment, the external stimulus is selected from the group consisting of electromagnetic waves, such as light, and sound waves, such as ultrasound.

In one embodiment, the protamine:RNA mass ratio is in the range of from 16:1 to 1:2, preferably in the range of from 8:1 to 1:2, more preferably in the range of from 4:1 to 1:2.

In one embodiment, the particle has a size in the range of from 10 nm to 990 nm, preferably of from 50 nm to 990 nm. In another embodiment, the particle has a size in the range of from 10 nm to 450 nm, preferably of from 50 nm to 450 nm. In yet another embodiment, the particle has a size in the range from 450 nm to 990 nm.

In one embodiment, the RNA is selected from the group consisting of messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers, preferably from the group consisting of mRNA, siRNA, shRNA, miRNA, antisense RNA, isRNA and RNA aptamers.

In one embodiment, the EDA is a polyanion and is provided in the form of a particle comprising the EDA and a polycation, wherein, preferably, the particle does not comprise RNA.

In one embodiment, the polyanion is a polymer of acrylic acid or substituted acrylic acid, preferably poly(2-propylacrylic acid), and/or the polycation is protamine.

In another aspect, the present invention relates to a particle comprising (i) at least one endosome destabilizing agent (EDA) being a polyanion and (ii) at least one polycation, wherein, preferably, the particle does not comprise RNA.

In one embodiment, the polyanion is a polymer of acrylic acid or substituted acrylic acid, preferably poly(2-propylacrylic acid), and/or the polycation is protamine.

In another aspect, the present invention relates to a pharmaceutical composition or kit comprising a first particle comprising protamine and RNA, preferably as defined above, and a second particle comprising (i) at least one endosome destabilizing agent (EDA) being a polyanion and (ii) at least one polycation, wherein, preferably, the second particle does not comprise RNA.

In one embodiment, the polyanion is a polymer of acrylic acid or substituted acrylic acid, preferably poly(2-propylacrylic acid), and/or the polycation is protamine.

In yet another aspect, the present invention relates to a kit comprising a particle comprising protamine and RNA, preferably as defined above, and at least one endosome destabilizing agent (EDA), preferably as defined above, in separate containers.

In one embodiment, the kit further comprises instructions for use of the kit in a method of treatment or prevention of a disease or for use of the kit in a method of immunostimulation, wherein, preferably, the method is as defined above.

BRIEF DESCRIPTION OF THE DRAWINGS

Other objects, advantages and novel features of the present invention will become apparent from the following detailed description when considered in conjunction with the accompanying drawings.

Peptides from Influenza hemagglutinin, namely peptide 1, GLFEAIEGFIENGWEGMIDGWYG (SEQ ID NO: 1), and peptide 2, GLFEAIEGFIENGWEGLAEALAEALEALAAGGSC (SEQ ID NO: 2; see FIG. 1A), as well as poly(2-propylacrylic acid) (MW: 8423.

DETAILED DESCRIPTION OF THE INVENTION

Figure 1A:
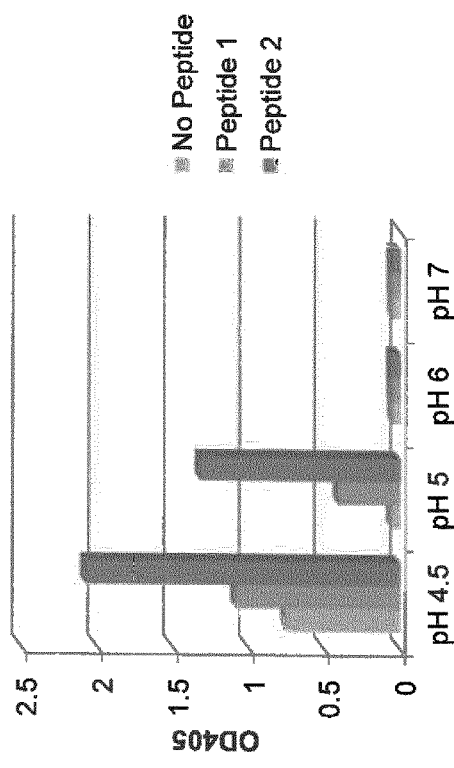
FIG. 1: Peptides from Influenza hemagglutinin and poly(2-propylacrylic acid) can destabilize cell membranes at a pH below 6
FIG. 1B) were diluted to 1 mg/ml using pure water and for poly(2-propylacrylic acid) using adequate addition of NaOH. Six micrograms of peptides (6 microliters) or 8 micrograms of poly(2-propylacrylic acid) (8 microliters) were placed in wells from U-bottom 96-well plates. Then, 200 microliters of a solution of PBS adjusted at pH 7, 6, 5 or 4.5 and containing 3 million fresh human red blood cells were added. Plates were left at 37° C. in a humidified $CO_2$ incubator for 7 hours (FIG. 1A) or 20 hours (FIG. 1B). Then 50 (FIG. 1A) or 80 (FIG. 1B) microliters of supernatant were transferred in a flat bottom 96-well plate, and OD 405 nm was recorded as a surrogate of hemoglobin content. The experiment highlights that at a pH below 6, Influenza hemagglutinin peptides 1 and 2 as well as poly(2-propylacrylic acid) damages red blood cells, i.e. destabilizes cell membranes. Peptide 2 is more efficacious than peptide 1.
Figure 1B:
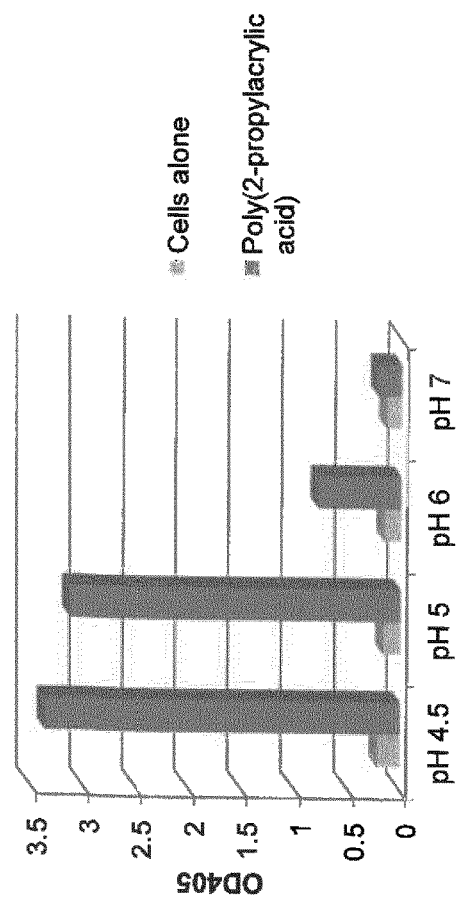
Figure 2:
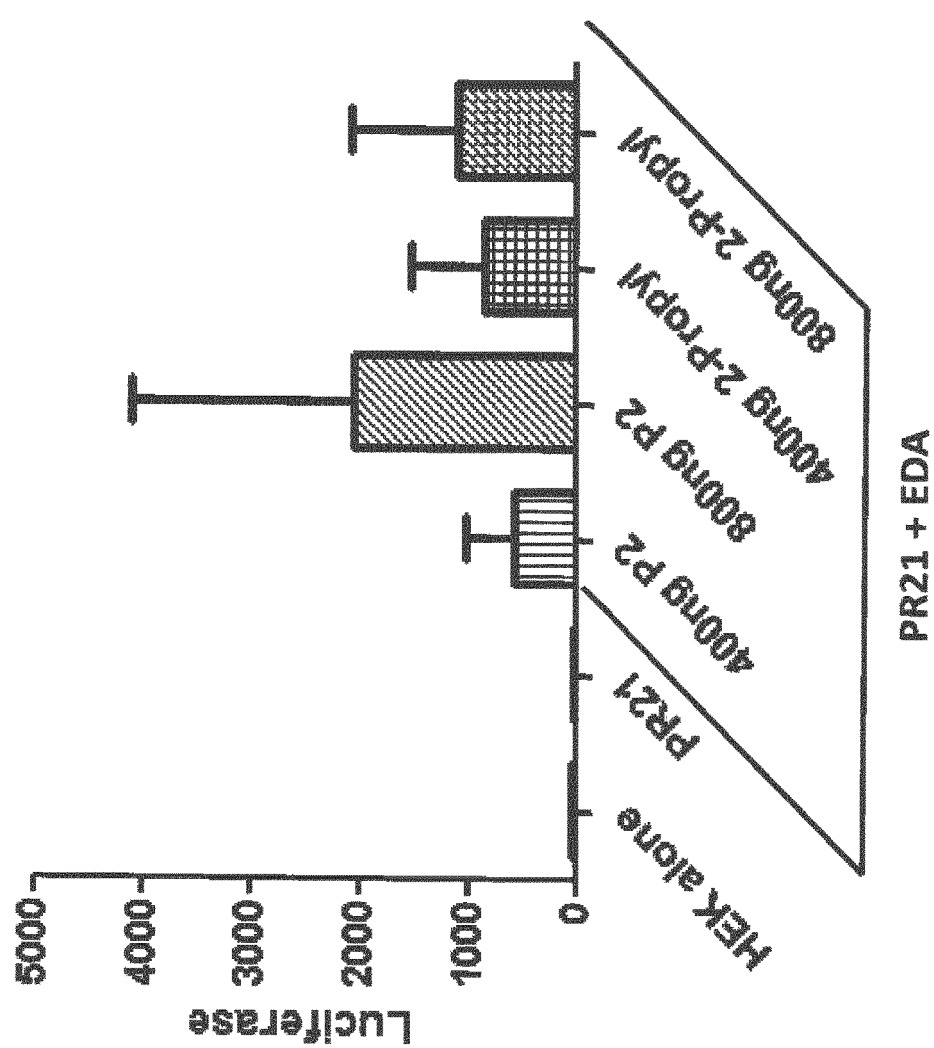
FIG. 2: Particles comprising RNA, protamine and an endosome destabilizing agent can transfer RNA into the cytosol A master mix of protamine and mRNA was made by mixing 7 micrograms of mRNA encoding luciferase at 1 mg/ml in water with 14 microliters of protamine Ipex 5000 diluted at 1 mg/ml in water. The preparation was diluted using 49 microliters of phosphate buffered saline (PBS). Two microliters (equivalent to 0.2 micrograms of mRNA mixed with 0.4 micrograms of protamine) were distributed in wells of a flat bottom white 96-well plate ("PR21"). Eventually 400 ng (0.4 microliters) or 800 ng (0.8 microliters) of EDA were added: either Influenza hemagglutinin peptide 2 ("P2") or poly(2-propylacrylic acid) ("2-Propyl"), both at 1 mg/ml in water. Then, 200 microliters of HEK cells at 5 million per ml in complete medium (RPMI plus 10% Fetal Calf Serum plus penicillin and streptomycin) were added. The plate was incubated 18 hours at 37° C. in a humidified 5% $CO_2$ incubator. Then, 100 microliters of cell culture supernatant were removed and 100 microliters of Bright-Glo™ substrate (Promega) were added. Luciferase activity was recorded using an infinite 200 (Tecan) system. The graph shows average and deviation in triplicate experiments. The results demonstrate that although, as it is known, protamine-mRNA particles of certain mass ratio diluted in PBS do not allow expression of the mRNA ("PR21": protamine-mRNA particles alone), addition of an EDA on the particles allows expression of the mRNA. Since peptide 2 and poly(2-propylacrylic acid) are negatively charged at neutral pH, it can be assumed that they coat the protamine-RNA nanoparticles made using a two-fold mass excess of protamine over RNA and thus being positively charged, without, however, wishing to be bound to this particular theory. Such EDA-coated protamine-RNA particles are taken up by cells, and, once in endosomes, the low pH activates/triggers the membrane destabilizing activity of the EDA that results in the release of the protamine-RNA particle in the cytosol where mRNA can be uncoated and translated by ribosomes.
Figure 3:
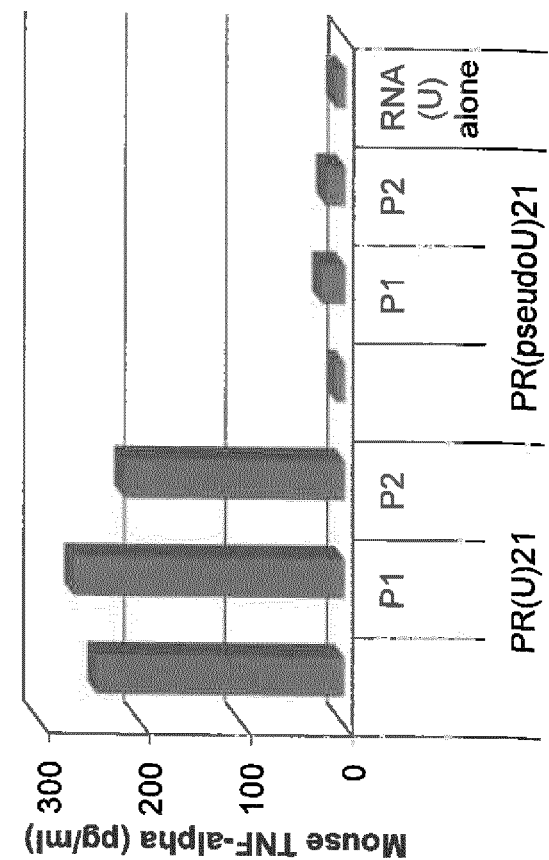
FIG. 3: Particles comprising RNA, protamine and an endosome destabilizing agent can be immunostimulating or non-immunostimulating mRNA encoding firefly luciferase was prepared using in vitro transcription in the presence of the four unmodified canonic residues (G, A, C and U) or in presence of a nucleotide mixture containing canonic G, A, C and pseudouridine (pseudoU) instead of uridine. For unmodified ("PR(U)21") as well as fully pseudouridine ("PR(pseudo)21") mRNA, master mixes of protamine-mRNA were made by mixing 1 microgram of luciferase coding mRNA at 1 mg/ml in water with 2 microliters of protamine diluted at 1 mg/ml in water. The preparations were diluted using 7 microliters of PBS. Two microliters (equivalent to 0.2 micrograms of mRNA mixed with 0.4 micrograms of protamine) were distributed in wells from a U bottom 96-well plate. Eventually, 800 ng (0.8 microliters) of EDA were added: either Influenza hemagglutinin peptide 1 ("P1") or peptide 2 ("P2"), both at 1 mg/ml in pure water. Then, 200 microliters of fresh mouse splenocytes at 5 million per ml in complete medium (RPMI plus 10% Fetal Calf Serum plus penicillin and streptomycin) were added. The plate was incubated 18 hours at 37° C. in a humidified 5% $CO_2$ incubator. Then, 50 microliters of cell culture supernatant were removed and added in 50 microliters of ELISA diluent in a mouse TNF-alpha ELISA assay (eBioscience). The graph shows mouse TNF-alpha contents in the supernatants (TNF-alpha content was evaluated using dilution of a provided standard). As negative control, splenocytes cultured in the presence of RNA (containing U residues) alone was used ("RNA(U) alone"). The results demonstrate that similarly to protamine-RNA particles, protamine-RNA-EDA particles (with the P1 or P2 peptide) are immunostimulating as long as the RNA contains adequate residues such as unmodified U residues. This formulation is particularly relevant for mRNA vaccination (expression of the mRNA together with innate immunostimulation). Non-immunostimulating RNA, such as pseudouridine containing RNA, can be used in the protamine-RNA-EDA particles if immunostimulation is not desired, such as it is usually the case for delivery of, for example, siRNA, aptamers, mRNA for gene therapy or antisense oligonucleotides.

In the following, definitions will be provided which apply to all aspects of the present invention.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, $2^{nd}$ Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention provides a particle comprising protamine, RNA and at least one endosome destabilizing agent (EDA).

Particles of the present invention preferably have a size in the range of from 10 nm to 990 nm, preferably of from 50 nm to 990 nm. In another embodiment, the particles have a size in the range of from 10 nm to 450 nm, preferably of from 50 nm to 450 nm. In yet another embodiment, the particles have a size in the range of from 450 nm to 990 nm.

The term "size" refers to the average size of the particles and is generally the "design size" or intended size of the particles prepared according to an established process. Size may be a directly measured dimension, such as the average or maximum diameter, or may be determined by an indirect assay such as a filtration screening assay. Direct measurement of particle size is typically carried out by dynamic light scattering. As minor variations in size arise during the manufacturing process, a variation up to 40% of the stated measurement is acceptable and considered to be within the stated size. Alternatively, particle size may be determined by filtration screening assays. For example, a particle preparation is less than a stated size, if at least 97% of the particles pass through a "screen-type" filter of the stated size.

In accordance with the present invention, the particles of the invention may further comprise on their outer surface a targeting agent which can selectively or preferably deliver the particles to a target cell population, and/or to a target organ or tissue. Such targeting may promote efficient drug uptake into cells and enhance efficacy. One targeting means which has been explored employs antibodies attached covalently or through electrostatic interactions to particle surfaces. Thus, in one embodiment, the particles of the invention may comprise a ligand for site specific targeting, such as an antibody. The ligand may be capable of binding to a disease-associated antigen such that the particle when administered accumulates at a diseased organ or tissue characterized by cells expressing the disease-associated antigen and preferably being characterized by association of the disease-associated antigen with their cell surface, e.g. the disease-associated antigen is a transmembrane protein. The disease-associated antigen may be a tumor-associated antigen and is preferably associated with the surface of a diseased cell, such as a tumor cell but preferably not with the surface of a healthy cell. Preferably the ligand for site specific targeting binds to an extracellular portion of the disease-associated antigen.

According to the invention, protamine is used as a cationic carrier agent. The term "protamine" refers to strongly basic nuclear proteins ("protamines") of relatively low molecular weight that are rich in arginine and are found associated especially with DNA in place of somatic histones in the sperm cells of various animals (such as fish). In particular, the term "protamine" refers to proteins found in fish sperm that are strongly basic, are soluble in water, are not coagulated by heat, and yield chiefly arginine upon hydrolysis. Protamines have been used in a long-acting formulation of insulin and to neutralize the anticoagulant effects of heparin.

The term "protamine", as used herein, is meant to comprise any protamine amino acid sequence obtained or derived from native or biological sources including fragments thereof and multimeric forms of said amino acid sequence or fragments thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine. In a preferred embodiment, the protamine source used for the production of the particles of the invention is protamine 5000 (5000 heparin-neutralizing units per ml) which contains protamine at more than 10 mg/ml in an isotonic salt solution, which may be further diluted.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the invention, "RNA" refers to single-stranded RNA or double stranded RNA and includes messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers. In a preferred embodiment, the RNA is selected from the group consisting of mRNA, siRNA, shRNA, miRNA, antisense RNA, isRNA and RNA aptamers.

The RNA may contain self-complementary sequences that allow parts of the RNA to fold and pair with itself to form double helices. According to the invention preferred as RNA are synthetic oligonucleotides of 6 to 100, preferably 10 to 50, in particular 15 to 30 or 15 to 20 nucleotides or messenger RNA (mRNA) of more than 50 nucleotides, preferably of 50 to 10,000, preferably 100 to 5000, in particular 200 to 3000 nucleotides.

According to the present invention, the term "messenger RNA (mRNA)" relates to a "transcript" which may be generated by using a DNA template and may encode a peptide or protein. Typically, an mRNA comprises a 5'-untranslated region, a protein coding region, and a 3'-untranslated region. In the context of the present invention, mRNA may be generated by in vitro transcription from a DNA template. The in vitro transcription methodology is known to the skilled person. For example, there is a variety of in vitro transcription kits commercially available.

According to the present invention, the term "small inhibitory RNA (siRNA)" relates to double stranded short (typically 19-23, preferably 21 nucleotides in length) oligonucleotides that can be used to induce the destruction of a target mRNA through the recognition of the target by one strand of the siRNA, a mechanism referred to as RNA interference (RNAi).

The term "small hairpin RNA (shRNA)" relates to a sequence of RNA that makes a tight hairpin turn and can be used to silence target gene expression via RNAi.

The terms "microRNA" or "miRNA" relate to a small non-coding RNA molecule (typically 19-25 nucleotides in length), which functions in transcriptional and post-transcriptional regulation of gene expression.

According to the present invention, the term "antisense RNA" relates to a single stranded RNA, usually a synthetic oligonucleotide that is designed to base-pair with a targeted cellular mRNA, thereby inhibiting physically the process of translation and eventually inducing destruction of the targeted mRNA.

According to the present invention, "immunostimulating RNA (isRNA)" relates to RNA that can activate innate immune receptors, such as, for example, the endoplasmic TLR-3, 7 and 8 or the cytosolic protein RIG-1. In one embodiment, the isRNA comprises one or more uridine (U) nucleotides.

According to the present invention, the term "RNA aptamer" relates to RNA that through its precise three dimensional structure can be used as an antibody, i.e., made to bind specifically to determined structures and thereby activate or block biological mechanisms.

According to the invention, the RNA may be modified. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or non-naturally occurring (synthetic) ribonucleotides in order to increase its stability and/or decrease cytotoxicity and/or modulate its immunostimulating potential. For example, in one embodiment, in the RNA used according to the invention uridine is substituted partially or completely, preferably completely, by pseudouridine.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The RNA may comprise further modifications. For example, a modification of mRNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

If, according to the present invention, it is desired to decrease stability of RNA, it is also possible to modify RNA so as to interfere with the function of elements as described above increasing the stability of RNA.

According to the present invention, RNA may be obtained by chemical synthesis or by in vitro transcription of an appropriate DNA template. In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably, cloning vectors are used for producing transcripts which generally are designated transcription vectors.

The term "translation" according to the invention relates to the process in the ribosomes of a cell by which a strand of messenger RNA directs the assembly of a sequence of amino acids to make a peptide or protein.

The term "inhibition of gene expression" relates to a process, wherein RNA oligonucleotides (e.g., single stranded antisense or double stranded siRNA) can be used to bind specific mRNA sequences inducing either the degradation of the targeted mRNA and/or to the blockade of translation.

According to the present invention, the protamine:RNA mass ratio is preferably 1:2 or higher (e.g., 1:1, 2:1 or 4:1). In one embodiment, the particles of the invention have a protamine:RNA mass ratio in the range of from 16:1 to 1:2, preferably in the range of from 8:1 to 1:2, more preferably in the range of from 4:1 to 1:2. In a particularly preferred embodiment, the particles of the invention have a protamine:RNA mass ratio in the range of from 4:1 to 1:1. In one embodiment, the particles of the invention have a protamine:RNA mass ratio of 2:1.

The term "endosome destabilizing agent (FDA)", as used herein, refers to an agent having an "endosome destabilizing activity", wherein such "endosome destabilizing activity" may be based on a mechanism such as destabilization of the endosomal membrane by pore formation, partial solubilization or even disruption. The EDA might act, for example, by direct insertion into the endosomal membrane or indirectly by either affecting molecules that are critical for the maintenance of the integrity of the endosomal membrane or by inducing osmotic rupture ("proton sponge effect").

In one embodiment, the endosome destabilizing activity of the FDA is triggered by an external stimulus. The term "external stimulus", as used herein, refers to a stimulus to which particles of the invention are exposed. It may, for example, be a change of the intracellular environment (e.g., a change of the pH value) or a stimulus selected from the group consisting of electromagnetic waves, such as light, and sound waves, such as ultrasound. In one embodiment, the external stimulus is a localized external stimulus.

In one embodiment, the EDA is selected from the group consisting of organic and inorganic molecules, polymers, lipids, inorganic nanoparticles and peptides.

Suitable organic molecules include compounds comprising tertiary amine groups and a hydrophobic chain; chloroquine, monensin; wortmannin; retinoic acid; and saponins.

Particularly preferred polymers include cationic polymers, such as polyethylenimine and poly(amidoamine)s; anionic polymers, such as polymers of acrylic acid or substituted acrylic acid (e.g., poly(2-propylacrylic acid)); charge-reversal copolymers; amphiphilic cationic copolymers; and pH-sensitive degradable polymers.

Suitable lipids include cationic lipids and zwitterionic lipids.

Suitable inorganic nanoparticles include layered double hydroxide nanoparticles, calcium phosphate nanoparticles, carbonate apatite nanoparticles, magnesium and manganous phosphate nanoparticles and calcium carbonate nanoparticles. In one embodiment, the inorganic nanoparticles are coated with lipids.

The term "peptide", as used herein, comprises naturally or non-naturally occurring oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids (e.g., 10 to 100, 10 to 50, 10 to 40, 20 to 100, 20 to 50 or 20 to 40 amino acids) joined covalently by peptide bonds. The term "protein" preferentially refers to large peptides, preferably to peptides with more than 100 amino acid residues, but in general the terms "peptide" and "protein" are synonyms and are used interchangeably herein. Particularly preferred peptides for use as EDA include KALA, GALA and hemagglutinin-derived peptides.

In one embodiment, the EDA is a pH-reactive agent. According to the present invention, the term "pH-reactive agent" refers to an agent having an endosome destabilizing activity which is triggered upon exposure to a particular pH or pH range. The endosome destabilizing activity may, for example, be triggered by a change of the structural conformation of the pH-reactive agent or by a pH-induced break of a pH-labile bond. The break of such bond may, for example, demask/activate an inherently endosomolytic agent. The endosome destabilizing activity may also be based on the proton sponge effect which is mediated by pH-reactive agents with a high buffering capacity and the flexibility to swell when protonated. Protonation induces a substantial influx of ions and water into the endosomal lumen that subsequently results in the osmotic rupture of the endosomal membrane.

In one embodiment, the endosome destabilizing activity of the pH-reactive agent is triggered by exposure to a pH in the range of from 4.0 to 6.5, preferably in the range of from 4.5 to 6.0, more preferably in the range of from 4.5 to 5.5.

In one embodiment, the pH-reactive agent is selected from the group consisting of polymers and peptides, preferably amphipathic polymers and peptides. Such polymers and peptides may, for example, change their structural conformation upon exposure to a particular pH or pH range. For example, the pH-reactive agent may be an amphipathic peptide, which changes its structural conformation from random coil at pH 7 to helical at a pH between 4.5 and 5.5.

In one embodiment, the polymers are polymers of acrylic acid or substituted acrylic acid, e.g., poly(2-propylacrylic acid). In one embodiment, the peptides are hemagglutinin-derived peptides, wherein, preferably, the hemagglutinin-derived peptides are Influenza hemagglutinin-derived peptides. In a particular embodiment, the peptide has a length of up to 100, preferably of up to 50, more preferably of up to 40 amino acids and comprises an amino acid sequence according to SEQ ID NO: 1 or SEQ ID NO: 2, preferably SEQ ID NO: 2. In one embodiment, the peptide has an amino acid sequence according to SEQ ID NO: 1 or SEQ ID NO: 2, preferably SEQ ID NO: 2

In one embodiment, the EDA is a photosensitizer, wherein, preferably, the endosome destabilizing activity of the photosensitizer is triggered by exposure to light. The term "photosensitizer", as used herein, refers to a molecule which upon absorption of light can be promoted to an excited state and undergo intersystem crossing with oxygen to produce reactive oxygen species, such as singlet oxygen. These reactive oxygen species then promote the destabilization/damage of the endosomal membrane, thereby releasing the entrapped particles of the present invention.

In one embodiment, the photosensitizer is selected from the group consisting of porphyrins, phthalocyanines, purpurins, chlorins, benzoporphyrins, lysomotropic weak bases, naphtalocyanines, cationic dyes, tetracyclines, pheophorbides, and derivatives or isomers thereof, wherein, optionally, the photosensitizer is conjugated to a carrier molecule, such as a polymer. Suitable derivatives or isomers include texaphyrins, porphycenes, bacteriochlorins, ketochlorins and hematoporphyrin derivatives. Particularly preferred photosensitizers are porphyrins and chlorins as well as derivatives or isomers thereof.

The present invention also provides methods for the preparation of particles according to the present invention.

In one embodiment, the method comprises the steps of:
(a) providing a solution of protamine;
(b) providing a solution of RNA;
(c) providing a solution of at least one endosome destabilizing agent (EDA); and
(d) combining the solutions obtained in steps (a) and (b) and adding the solution obtained in step (c).

In one embodiment, the solutions provided in steps (a), (b) and (c) are aqueous solutions.

Preferably, the above step (a) is carried out by diluting a solution of protamine, preferably an aqueous isotonic stock solution of protamine, preferably containing 1000 ("protamine 1000") to 5000 ("protamine 5000") heparin-neutralizing units per ml with a solution containing 0 to 125 mM electrolytes, preferably containing less than 100 mM, more preferably less than 50 mM and, in particular, less than 25 mM electrolytes. For example, protamine 1000 and 5000 stock solutions are commercially available from MEDA (Meda AB, Box 906, SE-170 09 Solna, Sweden) under the trademarks Protamin® Ipex 1000 and 5000, respectively.

Preferably, the above step (b) is performed by resuspending an appropriate amount of dried RNA in an aqueous solution containing 0 to 125 mM electrolytes, preferably containing less than 100 mM, more preferably less than 50 mM and, in particular, less than 25 mM electrolytes.

In one embodiment, particles of the present invention comprising protamine, RNA and EDA are prepared by diluting all three ingredients to less than 5 mg/ml, preferably to 1 mg/ml or less, in an aqueous solution containing 0 to 125 mM electrolytes, preferably in deionized water (herein also referred to as "pure water"). In one embodiment, (i) protamine is formulated as a 1 mg/ml solution by diluting a pharmaceutical isotonic solution of at least 10 mg/ml protamine 5000 with pure water; and (ii) RNA is formulated as a 1 mg/ml solution by resuspending dried RNA in pure water; and (iii) these preparation are mixed at a protamine:RNA mass ratio (here: volume ratio) of 2:1; and (iv) an EDA preparation at 1 mg/ml in water is added to the diluted protamine-RNA particle formulation.

In one embodiment, the method according to the present invention comprises the following steps:
(a) providing an aqueous solution of less than 5 mg/ml protamine by diluting an aqueous isotonic stock solution containing 5000 heparin-neutralizing units of protamine per ml with an aqueous solution containing 0 to 125 mM electrolytes;
(b) providing an aqueous solution of RNA at less than 5 mg/ml in an aqueous solution containing 0 to 125 mM electrolytes;
(c) providing an aqueous solution of EDA at less than 5 mg/ml in an aqueous solution containing 0 to 125 mM electrolytes;
(d) combining the solutions obtained in steps (a) and (b); and
(e) combining the solutions obtained in steps (d) and (c).

In the context of the present invention the terms "salt(s)" and "electrolyte(s)" are used interchangeably and mean a compound that at least partially dissociates into its respective counter ions in water.

According to the present invention, the term "mM electrolytes" means the concentration in $10^{-3}$ mol per liter of the sum of all electrolytes (including inorganic salts such as NaCl, KCl, $NaH_2PO_4$, $Na_2HPO_4$, $KH_2PO_4$, $K_2HPO_4$, $MgCl_2$, $MnCl_2$, $Na_2SO_4$, $K_2SO_4$, $MgSO_4$ and salts such Tris-HCl, EDTA, Hepes, etc.) in the solutions used to resuspend or to dilute the RNA stock solutions, in the solutions used to dilute a protamine stock solution (such as protamine 1000 or 5000) and in the solution used to dilute or resuspend an EDA before mixing the components.

The present invention also relates to a pharmaceutical composition or kit comprising particles of the invention and optionally one or more pharmaceutically acceptable carriers, diluents and/or excipients.

The pharmaceutical compositions of the invention are preferably sterile and contain an effective amount of the particles of the invention. The pharmaceutically composi-tions may also comprise further agents as discussed herein, such as an additional therapeutic agent or antigen.

Pharmaceutical compositions are usually provided in a uniform dosage form and may be prepared in a manner known in the art. The pharmaceutical composition of the invention may, e.g., be in the form of a solution or suspension.

The pharmaceutical composition of the invention may comprise salts, buffer substances, preservatives, carriers, diluents and/or excipients all of which are preferably pharmaceutically acceptable. The term "pharmaceutically acceptable" refers to the non-toxicity of a material which does not interfere with the action of the active component(s) of the pharmaceutical composition.

Salts which are not pharmaceutically acceptable may be used for preparing pharmaceutically acceptable salts and are included in the invention. Pharmaceutically acceptable salts of this kind comprise, in a non-limiting way, those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition of the invention include acetic acid in a salt, citric acid in a salt, boric acid in a salt and phosphoric acid in a salt.

Suitable preservatives for use in the pharmaceutical composition of the invention include benzalkonium chloride, chlorobutanol, paraben and thimerosal.

The term "carrier" refers to an organic or inorganic component, of a natural or non-natural (synthetic) nature, with which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are, e.g., sterile water, glucose solutions, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers.

The term "excipient" when used herein is intended to indicate all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The particles and pharmaceutical compositions described herein may be administered via any conventional route, such as by parenteral administration including by injection or infusion. Administration is preferably parenterally, e.g. intravenously, intraarterially, subcutaneously, in the lymph node, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of these parameters. In the case that a reaction in a patient is insufficient with an initial dose, higher doses (or effectively higher doses achieved by a different, more localized route of administration) may be used.

The pharmaceutical compositions of the invention may also comprise an immunomodulating agent such as anti-CTL-A4 or anti-regulatory T-cell reagents such as an anti-CD25 antibody or cyclophosphamide or an adjuvant. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical compositions of the present invention.

As used herein, the term "kit" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents. Said data carrier may be a non-electronic data carrier, e.g., a graphical data carrier such as an information leaflet, an information sheet, a bar code or an access code, or an electronic data carrier such as a floppy disk, a compact disk (CD), a digital versatile disk (DVD), a microchip or another semiconductor-based electronic data carrier. The access code may allow the access to a database, e.g., an internet database, a centralized, or a decentralized database. Said data carrier may comprise instructions for the use of the kit in the methods of the invention. In addition, the data carrier may comprise information or instructions on how to carry out the methods of the present invention.

The present invention also relates to particles as defined herein or the pharmaceutical compositions or kits as defined herein for use in a method of treatment or prevention of a disease or for use in a method of immunostimulation. The present invention further relates to particles as defined herein or kits as defined herein for use in a method of transfection, in particular transfection of cells with RNA.

It is demonstrated herein that particles of the present invention lead to the efficient release of RNA in the cytosol, allowing biological activities of RNA such as protein expression, interference with gene expression, or immunostimulation. Therefore, the particles, pharmaceutical compositions and kits of the present invention are useful to interfere with gene expression (e.g. by delivering antisense RNA or siRNA), modify protein activities (e.g. by delivering RNA aptamers), complement a deficient gene (e.g. by delivering non-immunostimulating mRNA) or activate immunity (e.g. by delivering isRNA or mRNA vaccines) in certain disease states, in particular in the case of chronic diseases, such as cancer, infectious diseases, allergies and autoimmune diseases. Thus, the particles and pharmaceutical composition of the present invention are particularly useful in the treatment of said diseases.

According to the present invention, the RNA can be coding RNA, i.e. RNA encoding a peptide or protein, such as a pharmaceutically active peptide or protein. Said RNA may express the encoded peptide or protein. For example, said RNA may be RNA encoding and expressing an antigen, or a pharmaceutically active peptide or protein such as an immunologically active compound (which preferably is not an antigen). Alternatively, the RNA can be non-coding RNA such as antisense-RNA, micro RNA (miRNA) or siRNA.

According to the invention, the term "RNA encoding a peptide or protein" means that the RNA, if present in the appropriate environment, preferably within a cell, can direct the assembly of amino acids to produce the peptide or protein during the process of translation. Preferably, RNA according to the invention is able to interact with the cellular translation machinery allowing translation of the peptide or protein.

According to the invention, RNA comprises or consists of pharmaceutically active RNA. A "pharmaceutically active RNA" is a RNA that encodes a pharmaceutically active peptide or protein or is pharmaceutically active on its own, e.g., it has one or more pharmaceutical activities such as those described for pharmaceutically active proteins. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a $TH_2$ immune response, which is useful for treating a wide range of $TH_2$ mediated diseases. Immunologically active compounds can be useful as vaccine adjuvants. In one embodiment, the RNA forming a hydrophilic shell on at least a portion of the vesicular core of the particles of the present invention encodes an immunologically active compound. Said compound preferably does not encode an antigen.

If, according to the present invention, it is desired to induce or enhance an immune response by using particles as described herein, the immune response may be triggered or enhanced by the RNA. For example, proteins or peptides encoded by the RNAs or procession products thereof may be presented by major histocompatibility complex (MHC) proteins expressed on antigen presenting cells. The MHC peptide complex can then be recognized by immune cells such as T cells leading to their activation.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold). Examples of infectious diseases treatable with the particles and pharmaceutical composition of the present invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chlamydia or gonorrhea), gastric ulcer (*Helicobacter*), cholera (*Vibrio*), tuberculosis, diphtheria, infections by *E. coli, Staphylococci, Salmonella* or *Streptococci* (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*.

The particles and pharmaceutical composition of the present invention are also useful in treating allergies and autoimmune diseases. The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The particles and pharmaceutical compositions of the present invention can also be utilized to deliver RNA that may correct an inherited genetic disease such as cystic fibrosis or myopathies (e.g., by facilitating or blocking a particular biological activity). Similarly, the particles can be used to achieve production of therapeutic proteins (for example enzymes or recombinant antibodies) by the own cells of the treated patients.

The particles and pharmaceutical compositions of the present invention can also be used in conjunction with another therapeutic agent which can be administered prior to, simultaneously with or after administration of the particles or pharmaceutical compositions of the present invention. Such therapeutic agents include immunomodulating agents, which may be immunostimulating or immunosuppressive, chemotherapeutic drugs for cancer patients, e.g. gemcitabine, etopophos, cis-platin, carbo-platin, antiviral agents, anti-parasite agents or an anti-bacterial agents and, if administered simultaneously with the particles of the present invention, may be present in a pharmaceutical composition of the present invention.

The pharmaceutical compositions of the present invention may also be used in genetic vaccination, wherein an immune response is stimulated by introducing into a subject a suitable mRNA which codes for an antigen or a fragment thereof, e.g., a disease-associated antigen.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. In this embodiment, the particles and pharmaceutical compositions of the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I—presented peptides by transfection with nucleic acids encoding tumor antigens in vitro and administered to a patient. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, GASP-8, CDC27/m, CDK4/m, CEA, CLAUDIN-12, c-MYC, CT, Gyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the particles of the present invention comprises the steps of activation of antigen presenting cells, such as dendritic cells and/or macrophages, presentation of an antigen or fragment thereof by said antigen presenting cells and activation of cytotoxic T cells due to this presentation.

By "treat" it is meant to administer a compound or composition as described herein to a subject in order eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject", as used herein, preferably relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity, such as animals of zoos. In a preferred embodiment, the subject is a human.

The present invention further relates to a particle comprising protamine and RNA for use in a method of treatment or prevention of a disease or for use in a method of immunostimulation, the method comprising the steps of:
  (a) administering the particle to a subject in need thereof; and
  (b) administering at least one endosome destabilizing agent (EDA) to the subject and/or exposing the subject to an external stimulus which triggers the endosome destabilizing activity of the EDA or which destabilizes endosomes.

In one embodiment, the EDA is administered before or after the particle, preferably after the particle. In one embodiment, the particle and the EDA are administered by different routes, wherein, preferably, the particle is administered systemically and the EDA is administered topically, or vice versa. Systemic administration is the administration of a substance into the circulatory system of the subject, e.g. via enteral or parenteral administration. Topical administration is the delivery/administration of a substance directly to the site of action (also referred to as localized administration). In another embodiment, the EDA is administered simultaneously with the particle, wherein, preferably, the EDA and the particle are administered by the same route.

In one embodiment, the EDA is as defined above. In one embodiment, the EDA, preferably the EDA as defined above, is formulated (vectorized), e.g. by using a targeting agent and/or a protecting agent. Preferably, a targeting agent used for vectorization of the EDA is as described above. In one embodiment, the targeting agent is an agent which allows the selective or preferred delivery of the EDA to a target cell population and/or to a target organ or tissue. In one embodiment, the targeting agent is an antibody, peptide or small ligand. Preferably, a protecting agent used for vectorization of the EDA is an agent which increases the (in vivo) stability and/or (in vivo) half life and/or bioavailability of the EDA. Suitable protecting agents include compounds that form (nano-)particles with the EDA and/or that encapsulate the EDA and may, for example, include excipients as defined above. The targeting agent and/or protecting agent may also be used to solubilize the EDA.

In one embodiment of the above method, the EDA is a polyanion and is provided in the form of (i.e. formulated as) a particle comprising the EDA and a polycation, wherein, preferably, the particle does not comprise RNA.

The term "polyanion", as used herein, refers to molecules or chemical complexes having negative charges at several sites. The term "polycation", as used herein, refers to molecules or chemical complexes having positive charges at several sites. In one embodiment, the polyanion is a polymer of acrylic acid or substituted acrylic acid and/or the polycation is protamine. In one embodiment, the polymer of acrylic acid or substituted acrylic acid is poly(2-propylacrylic acid).

In one embodiment, the particle has a size in the range of from 10 nm to 990 nm, preferably of from 50 nm to 990 nm. In another embodiment, the particle has a size in the range of from 10 nm to 450 nm, preferably of from 50 nm to 450 nm. In yet another embodiment, the particle has a size in the range of from 450 nm to 990 nm. The particle may further comprise (e.g. be coated with) a targeting agent as described above. In one embodiment, the particle is administered systemically (e.g. intravenously). In one embodiment, the particle is administered before, simultaneously with or after the particle comprising protamine and RNA, preferably simultaneously with the particle comprising protamine and RNA. In one embodiment, the particles are administered via the same route.

The present invention also relates to a particle comprising (i) at least one endosome destabilizing agent (EDA) being a polyanion and (ii) at least one polycation, wherein, preferably, the particle does not comprise RNA. Preferably, the polyanion and/or the polycation and/or the particle size are as defined above.

The present invention further relates to a pharmaceutical composition or kit comprising a first particle comprising protamine and RNA, preferably as defined above, and a second particle comprising (i) at least one endosome destabilizing agent (EDA) being a polyanion and (ii) at least one polycation, wherein, preferably, the second particle does not comprise RNA. Preferably, the polyanion and/or the polycation and/or the particle size are as defined above.

The present invention also relates to a kit comprising a particle comprising protamine and RNA, preferably as defined above, and at least one endosome destabilizing agent (EDA), preferably as defined above, in separate containers. In one embodiment, the kit further comprises instructions for use of the kit in a method of treatment or prevention of a disease or for use of the kit in method of immunostimulation, wherein, preferably, the method is as defined above. In one embodiment, the kit further comprises instructions for use of the kit in a method of transfection, in particular transfection of cells with RNA.

Particles of the invention when contacted with appropriate cells or administered to a subject are capable of leading to the production of the protein encoded by the mRNA or to the inhibition of expression of the gene(s) targeted by the siRNA/antisense RNA or to the release in the cytosol of RNA aptamers contained in the particles.

Should they contain immunastimulating RNA (isRNA), particles of the invention when contacted with appropriate cells or administered to a subject are capable of inducing cytokines. Thus, the particles according to the invention are useful as a mRNA vaccine.

Should they contain non-immunostimulating RNA, particles of the invention when contacted with appropriate cells or administered to a subject do not induce cytokines. Thus, the particles according to the invention are useful for gene therapy (mRNA) or gene interference (antisense or siRNA) or protein inhibition (aptamer).

The present invention also relates to a method for simultaneously providing an antigen (encoded by an mRNA) and stimulating the innate immune system of a subject, the method comprising administering to the subject an effective amount of a particle or pharmaceutical composition of the present invention. The stimulation of the innate immune system preferably involves the stimulation of one or more of TLR-7, TLR-8 and TLR-3. A concomitant stimulation of the adaptive immune system (specific B- and T-lymphocytes) is possible thanks to the expression of the mRNA-encoded antigen.

The present invention also provides an ex vivo method for functional delivery of RNA into cells by contacting the cells with particles of the present invention. These transfected cells can be transferred into a subject, such as the subject from whom the cells were obtained, to operate the therapeutic function. In one embodiment, suitable cells are isolated from a subject and treated in vitro by adding to the isolated cells an effective amount of particles of the present invention. Afterwards, the transfected cells are (re-)introduced into the subject. Suitable cells for such ex vivo treatment include but are not limited to immune cells, such as dendritic cells, B-cells and natural killer (NK) cells.

The present invention also relates to the use of a particle as defined herein or of a pharmaceutical composition as defined herein in the manufacture of a medicament for the treatment or prevention of a disease or for use in a method of immunostimulation.

The present invention further relates to a method of treatment or prevention of a disease or to a method of immunostimulation, the methods comprising the step of administering a particle as defined herein or a pharmaceutical composition as defined herein to a subject in need thereof.

The present invention also relates to a method of treatment or prevention of a disease or to a method of immunostimulation, the methods comprising the steps of:
    (a) administering a particle comprising protamine and RNA to a subject in need thereof; and
    (b) administering at least one endosome destabilizing agent (FDA) to the subject and/or exposing the subject to an external stimulus which triggers the endosome destabilizing activity of the FDA or which destabilizes endosomes.

The following examples are intended to illustrate preferred embodiments of the invention and should not be interpreted to limit the scope of the invention as defined in the claims.

EXAMPLES

Example 1: Validation of EDA

Two peptides derived from Influenza virus hemagglutinin were chemically synthesized and resuspended in pure water at 2 mg/ml, peptide 1: GLFEAIEGFIENGWEGMIDGWYG (SEQ ID NO: 1) and peptide 2: GLFEAIEGFIENGWEG-LAEALAEALEALAAGGSC (SEQ ID NO: 2). Pure water is added on dried poly(2-propylacrylic acid) and dissolution is performed thanks to the addition of the required amount of 3M NaOH. The EDAs are further diluted to 1 mg/ml using pure water. Two to 10 micrograms are put in wells of a 96-well plate. Fresh human red blood cells are resuspended at 5 million per ml in PBS buffer pre-adjusted to 017, 6, 5 or 4.5 thanks to addition of the required amount of 1M citric acid. Two hundred microliters of cells are added on the EDA. The plates are left at 37° C. in a humidified $CO_2$ incubator. Six to 24 hours later, 50 or 80 microliters of supernatant are transferred to a flat 96-well plate. OD at 405 nm is measured using an ELISA reader. The FDA's efficacy correlates to its ability to lyse red blood cells (high hemoglobin content in the supernatant as evaluated by absorption at 405 nm) at acidic pH.

Example 2: Method for the Preparation of Protamine-RNA-EDA Particle Composition A messenger RNA coding for the protein luciferase is produced by in vitro transcription and purified by HPLC. The product is then lyophilized and resuspended at 1 mg/ml in pure water. Protamine® IPEX 5000 is diluted 14 times in pure water to provide a solution of protamine at approximately 1 mg/ml in low salt. The mRNA and the protamine are mixed at a mass ratio of twice more protamine than RNA. Immediate and intensive mixing is performed for example by pipetting up and down or by vortexing. Then, the particles are diluted ten times by addition of PBS. Then, Influenza hemagglutinin peptide 2 ("P2": GLFEAIEGFIEN-GWEGLAEALAEALEALAAGGSC, SEQ ID NO: 2) or poly(2-propylacrylic acid) ("2-Propyl") at 1 mg/ml in pure water are added in a mass amount identical to or double of the mass amount of protamine. Immediate and intensive mixing is performed for example by pipetting up and down or by vortexing. The formulation is left for a few minutes on the bench and may then be further diluted with an adequate solution. Should the protamine-RNA-EDA particle solution be too diluted, the particles can be recovered by centrifugation or freeze drying and be resuspended in the adequate volume of desired solution before being used. The amount of particle equivalent to 200 ng of RNA/400 ng of protamine/400 ng or 800 ng of EDA are put in a flat well of a white 96-well plate. Two hundred microliters of complete RPMI medium (10% FCS, Penicillin, Streptomycin) containing 1 million of HEK cells are added and the plate is incubated over night at 37° C. in a $CO_2$ incubator. The amount of luciferase activity is recorded by removing 100 microliters of supernatant, adding 100 microliters of luciferase substrate and recording immediately luminescence. The data demonstrate that although protamine-RNA particles do not generate detectable luciferase activity, the same particles mixed with EDA are capable of releasing functional RNA in the cytosol of cells as evidenced by luciferase activity.

Example 3: Method for the Preparation of Immunostimulating or Non-Immunostimulating Protamine-RNA-EDA Particle Composition Messenger RNAs coding for the protein luciferase are produced by in vitro transcription in the presence of canonic uridine or in the presence of pseudouridine. RNAs are then purified by HPLC, lyophilized and resuspended at 1 mg/ml in pure water. Protamine® IPEX 5000 is diluted 14 times in pure water to provide a solution of protamine at approximately 1 mg/ml in low salt. The mRNA and the protamine are mixed at a mass ratio of twice more protamine than RNA. Immediate and intensive mixing is performed for example by pipetting up and down or by vortexing. PBS is added so that RNA is at 0.1 mg/ml final and protamine at 0.2 mg/ml final. Then, Influenza hemagglutinin derived peptides 1 or 2 (P1: GLFEAIEGFIENGWEGMIDGWYG, SEQ ID NO: 1, and P2: GLFEAIEGFIENGWEGLAEALAEALEA-LAAGGSC, SEQ ID NO: 2) at 1 mg/ml in pure water are eventually added in a mass amount double of the mass amount of protamine. Immediate and intensive mixing is performed for example by pipetting up and down or by vortexing. An equivalent of 200 ng of RNA/400 ng of protamine/800 ng of EDA is added in a well of a 96-well plate with U bottom. Two hundred microliters of complete RPMI medium (10% FCS, penicillin-streptomycin) containing 5 million per ml of fresh splenocytes from BALB/c mouse are added. Cells incubated with uridine containing mRNA alone are used as negative control. The plate is incubated overnight in a humidified 37° C. $CO_2$ incubator. Innate immunostimulation is measured by quantifying in 50 microliters of cell culture supernatant the content in mouse TNF-alpha. The results show that particles made using uridine-containing RNA are immunostimulating through Toll-like Receptors while particles made using pseudouridine-containing RNA do not activate innate immune cells.

Example 4: Preparation of Protamine-EDA Particles

Figure 4A:
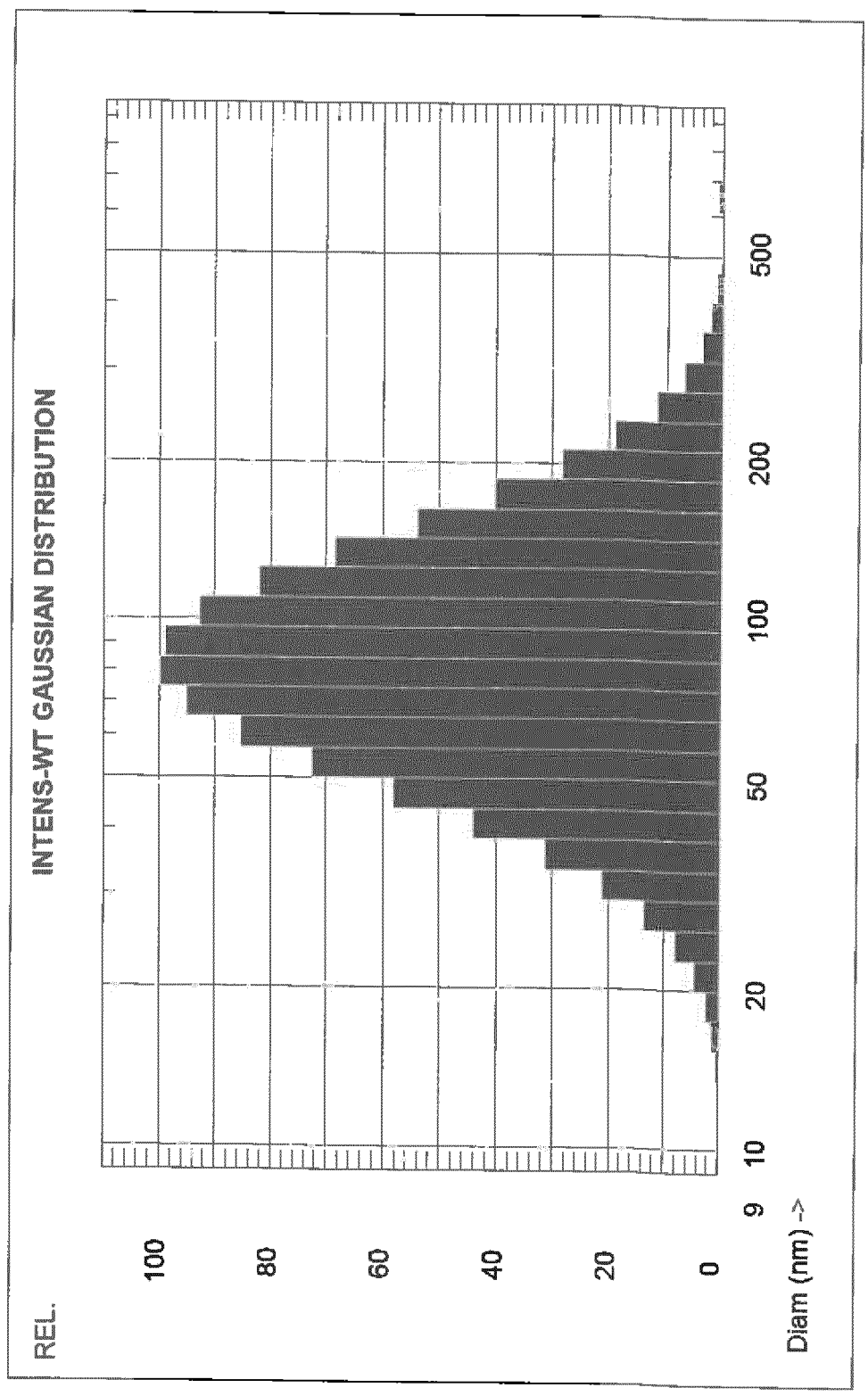
FIG. 4: Size distribution of particles made from a polyanionic endosome destabilizing agent and protamine Poly(2-propylacrylic acid) in solution was diluted to 0.1 mg/ml in water; protamine 5000 was diluted to 0.1 mg/ml in water. The protamine solution was added to an equal volume (i.e. equal mass amount) of poly(2-propylacrylic acid). The solution was homogenized by pipetting up and down. Particle size was evaluated using light scattering spectroscopy (PSS NICOMP, Particle sizing system, Santa Barbara, Calif., USA) and a viscosity of 0.933 (water solution). The particle size was distributed homogenously. The mean diameter was 96.5 nm (FIG. 4A). Poly(2-propylacrylic acid) in solution was diluted to 1 mg/ml in water; protamine 5000 was diluted to 1 mg/ml in water. The protamine solution was added to an equal volume (i.e. equal mass amount) of poly(2-propylacrylic acid). The solution was homogenized by pipetting up and down. A 5-fold volume excess of Glucose 5% was added. Particle size was evaluated using light scattering spectroscopy (PSS NICOMP, Particle sizing system, Santa Barbara, Calif., USA) and a viscosity setting of 1.066 (corresponding to Glucose 5%). The particle size was distributed heterogeneously. The mean diameter was 560.2 nm (FIG. 4B).
Figure 4B:
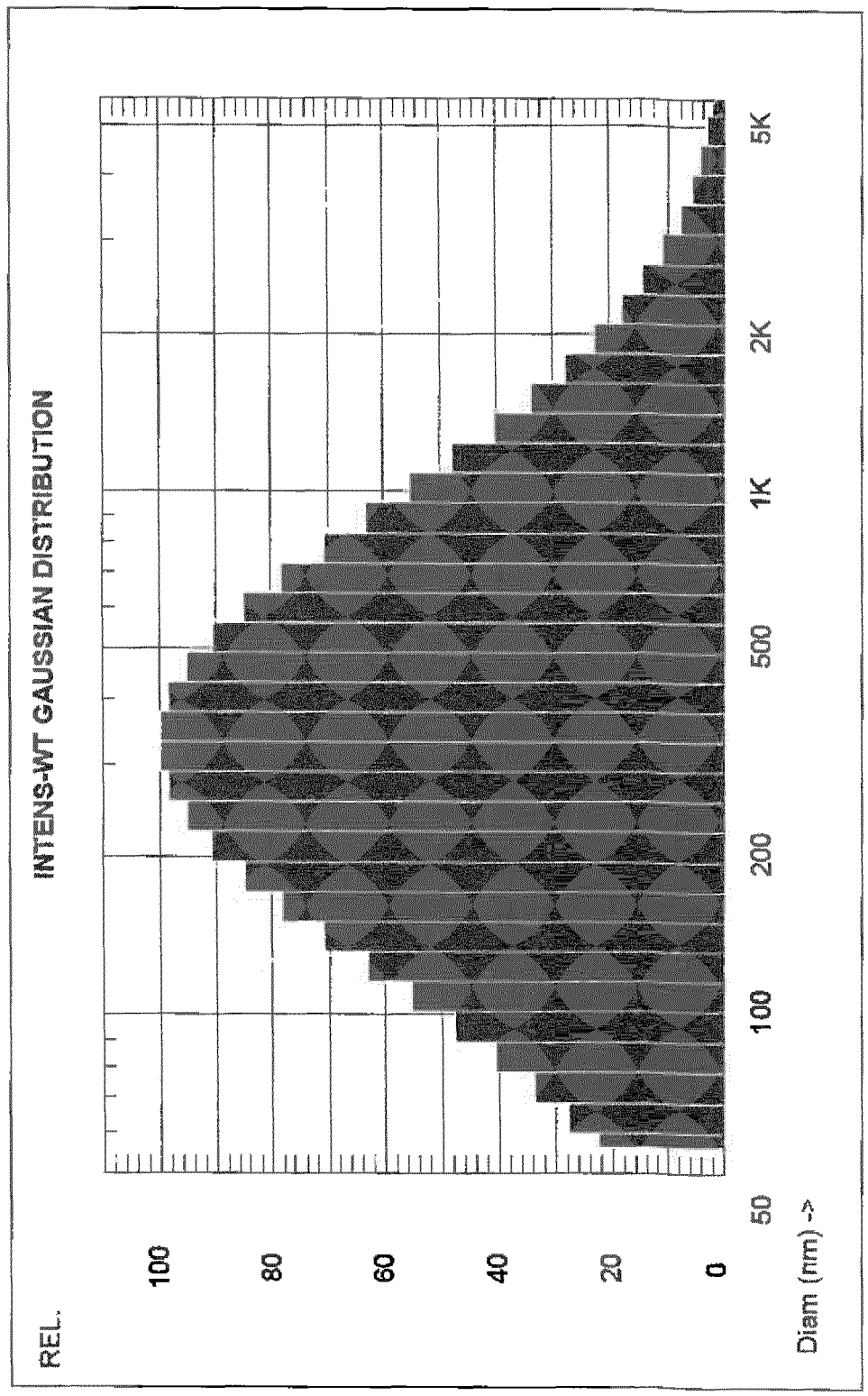

The polyanionic endosome destabilizing agent poly(2-propylacrylic acid) was diluted to 0.1 mg/ml in water, protamine 5000 was diluted to 0.1 mg/ml in water. The protamine solution was added to an equal volume (i.e. equal mass amount) of poly(2-propylacrylic acid). The solution was homogenized by pipetting up and down. Particle size was evaluated using light scattering spectroscopy (PSS NICOMP, Particle sizing system, Santa Barbara, Calif., USA) and a viscosity of 0.933 (water solution). The particle size was distributed homogenously. The mean diameter was 96.5 nm (FIG. 4A). Poly(2-propylacrylic acid) in solution was diluted to 1 mg/ml in water, protamine 5000 was diluted to 1 mg/ml in water. The protamine solution was added to an equal volume (i.e. equal mass amount) of poly(2-propylacrylic acid). The solution was homogenized by pipetting up and down. A 5-fold volume excess of Glucose 5% was added. Particle size was evaluated using light scattering spectroscopy (PSS NICOMP, Particle sizing system, Santa Barbara, Calif., USA) and a viscosity setting of 1.066 (corresponding to Glucose 5%). The particle size was distributed heterogeneously. The mean diameter was 560.2 nm (FIG. 4B). These results show that it is possible to form nanoparticles comprising a polyanionic EDA (e.g. poly(2-propylacrylic acid)) and a polycation (e.g. protamine).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

REFERENCES

Rettig L, Haen S P, Bittermann A G, von Boehmer L, Curioni A, Krämer S D, Knuth A, Pascolo S. Particle size and activation threshold: a new dimension of danger signaling. Blood. 2010 Jun. 3; 115(22):4533-41.
Fotin-Mleczek M, Duchardt K M, Lorenz C, Pfeiffer R, Ojkić-Zrna S, Probst J, Kallen K J. RNA-based vaccines with dual activity induce balanced TLR-7 dependent adaptive immune responses and provide antitumor activity. J Immunother. 2011 January; 34(1):1-15.

The invention claimed is:

1. A method of treating a disease or a method of immuno stimulation, comprising administering a particle to a subject in need thereof, wherein the particle comprises protamine 1000 or protamine 5000, RNA and at least one endosome destabilizing agent (EDA), wherein the EDA is a pH-reactive agent, wherein endosome destabilizing activity of the pH-reactive agent is triggered by exposure to a pH in the range of from 4.0 to 6.5, wherein the pH-reactive agent is selected from the group consisting of polymers and a peptide, wherein the polymers are polymers of acrylic acid or substituted acrylic acid and the peptide comprises influenza hemagglutinin peptide 2 according to SEQ ID NO: 2, and wherein the RNA is messenger RNA (mRNA).

2. The method of claim 1, wherein the protamine:RNA mass ratio is in the range of from about 16:1 to 1:2.

3. The method of claim 1, wherein the particle has a size in the range of from about 10 nm to 990 nm.

4. The method of claim 1, wherein the polymer of acrylic acid or substituted acrylic acid is poly(2-propylacrylic acid).

5. The method of claim 1, wherein the particle is administered in combination with another therapeutic agent, wherein the therapeutic agent is administrated prior to, simultaneously with, or after the administration of the particle.

6. The method of claim 1, wherein the particle is administered by an administration route selected from the group comprising: intravenous, intraarterial, subcutaneous, in the lymph node, intradermal or intramuscular adminitrations.

7. The method of claim 1, wherein the disease is a genetic disease.

8. The method of claim 7, wherein the genetic disease is a myopathy.

9. The method of claim 1, wherein the subject is human.

10. The method of claim 1, wherein the method is for immunostimulation and the RNA encodes a disease associated antigen.

11. The method of claim 7, wherein the genetic disease is cystic fibrosis.

12. The method of claim 1, wherein the disease is cancer.

13. The method of claim 1, wherein the disease is an infectious disease.

14. The method of claim 1, wherein the disease is an allergy.

15. The method of claim 1, wherein the disease is an autoimmune disease.

* * * * *